United States Patent
Li

(10) Patent No.: US 10,478,383 B2
(45) Date of Patent: Nov. 19, 2019

(54) STERILIZABLE DENTAL ROOL CANAL FILLING COMPOSITION, POINTS/CONES MADE OF SAME, AND PROCESS OF STERILIZING SAME

(71) Applicant: TULSA DENTAL PRODUCTS LLC, Tulsa, OK (US)

(72) Inventor: Nathan Y. Li, Malibu, CA (US)

(73) Assignee: DENTSPLY SIRONA Inc., York, PA (US)

(*) Notice: Subject to any disclaimer, the term of this patent is extended or adjusted under 35 U.S.C. 154(b) by 276 days.

(21) Appl. No.: 15/201,383

(22) Filed: Jul. 1, 2016

(65) Prior Publication Data
US 2017/0020790 A1 Jan. 26, 2017

Related U.S. Application Data

(60) Provisional application No. 62/187,751, filed on Jul. 1, 2015, provisional application No. 62/187,753, filed on Jul. 1, 2015.

(51) Int. Cl.
| | |
|---|---|
| *A61K 6/083* | (2006.01) |
| *A61K 6/00* | (2006.01) |
| *A61K 6/02* | (2006.01) |
| *A61L 2/00* | (2006.01) |
| *A61C 5/50* | (2017.01) |

(52) U.S. Cl.
CPC .............. *A61K 6/0038* (2013.01); *A61C 5/50* (2017.02); *A61K 6/0008* (2013.01); *A61K 6/0205* (2013.01); *A61L 2/0035* (2013.01); *A61L 2202/21* (2013.01)

(58) Field of Classification Search
CPC .................................................. A61K 6/0038
See application file for complete search history.

(56) References Cited

U.S. PATENT DOCUMENTS

| | | | |
|---|---|---|---|
| 4,950,697 A | * 8/1990 | Chang | ............... C08K 5/101 433/224 |
| 5,934,460 A | 8/1999 | Schmid | |
| 7,665,991 B1 | * 2/2010 | Kert | ........... A61O 5/50 433/102 |
| 8,043,093 B2 | 10/2011 | Shinozaki et al. | |
| 2004/0228898 A1 | 11/2004 | Ross et al. | |
| 2013/0337414 A1 | * 12/2013 | Li | ............ A61K 6/0038 433/224 |

OTHER PUBLICATIONS

International Search Report of Counterpart PCT International Application No. PCT/US2016/040885.

* cited by examiner

*Primary Examiner* — Michael F Pepitone
(74) *Attorney, Agent, or Firm* — Dentsply Sirona Inc.

(57) ABSTRACT

A root canal filling cone made of a material having a composition that can maintain its physical and chemical characteristics and shelf life after sterilization, and a process of sterilizing the point/cone prior to shipment to a user. In one aspect, the cone is made of a composition that includes a plurality of base polymers of substantially equal amounts, and nanoparticles, which can withstand sterilization by gamma irradiation. In one embodiment, the compound includes Gutta Percha based polymers. In another aspect, the Gutta Percha based cone is packaged and sterilized by irradiation prior to shipment to a user. In one embodiment of the present invention, the irradiation is gamma irradiation.

18 Claims, 7 Drawing Sheets

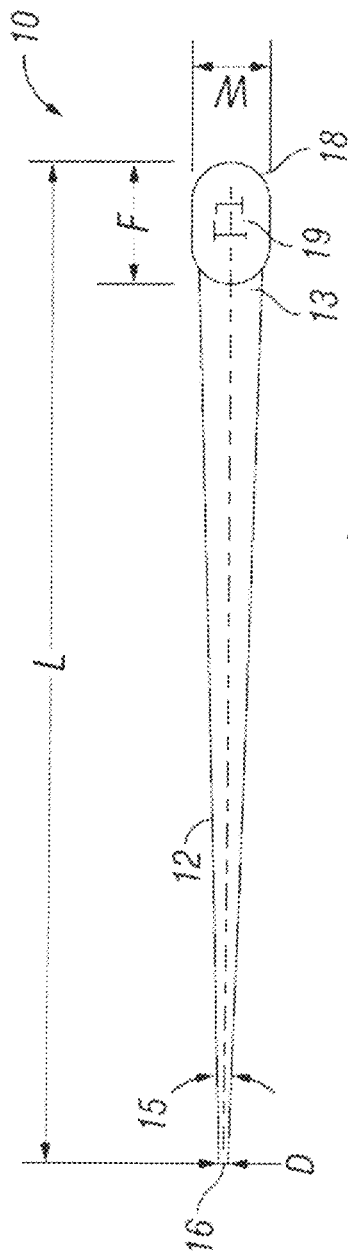
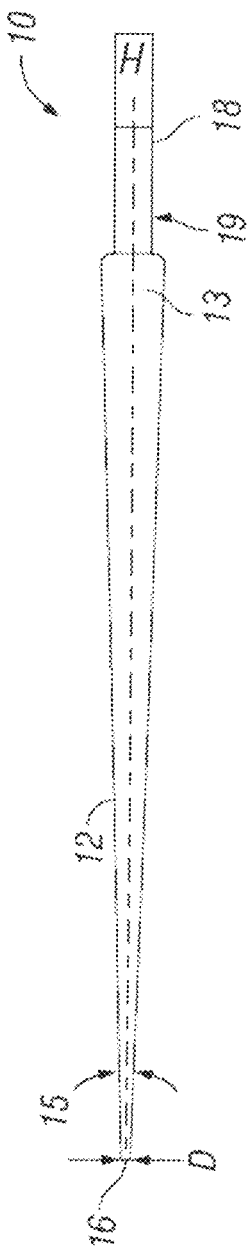
FIG. 1A
FIG. 1B

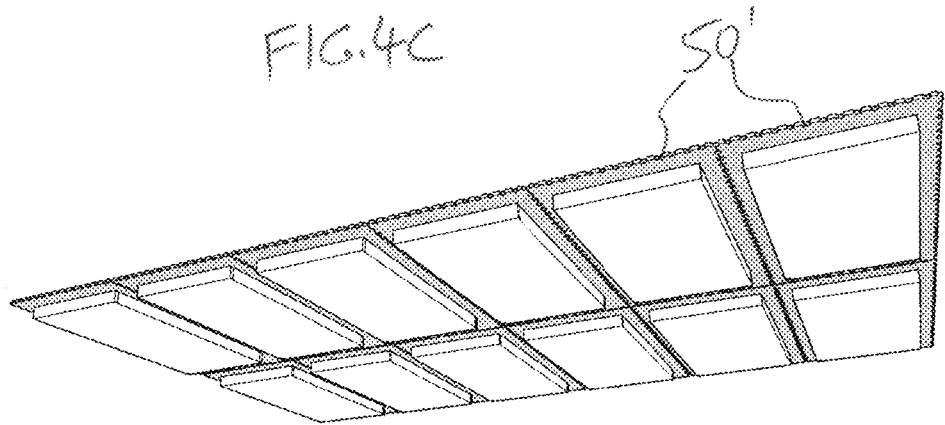
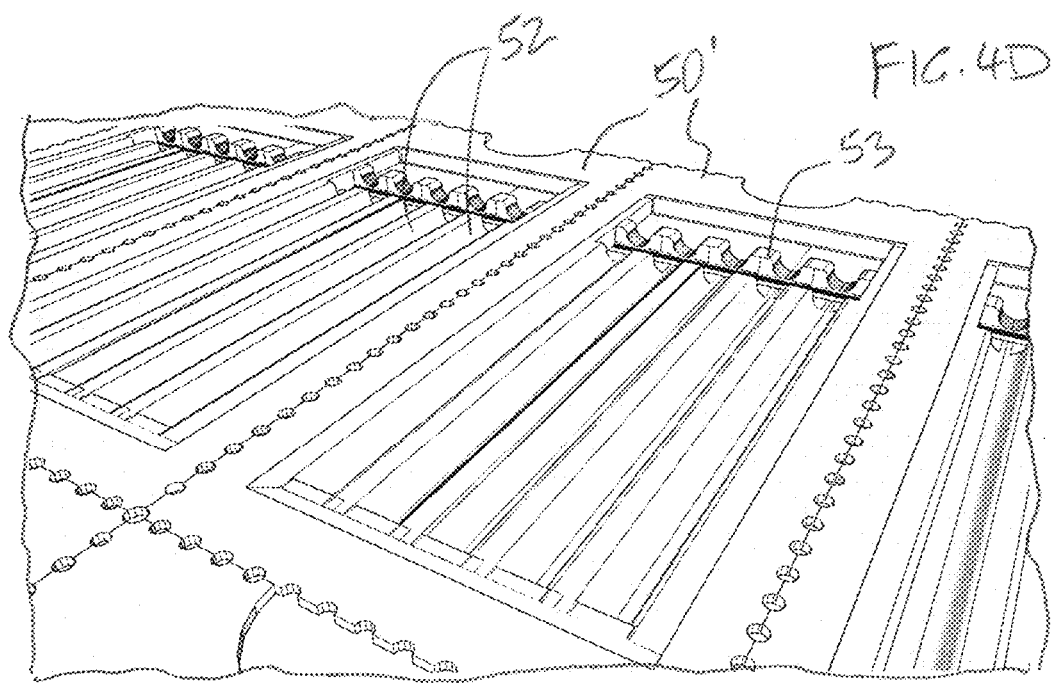

STERILIZABLE DENTAL ROOL CANAL FILLING COMPOSITION, POINTS/CONES MADE OF SAME, AND PROCESS OF STERILIZING SAME

PRIORITY CLAIM

This application claims the priority of U.S. Provisional Patent Application No. 62/187,751 filed on Jul. 1, 2015; and the priority of U.S. Provisional Patent Application No. 62/187,753 filed on Jul. 1, 2015. These provisional applications and all publications noted below are fully incorporated by reference as if fully set forth herein.

BACKGROUND OF THE INVENTION

Field of the Invention

The present invention is directed to materials for filling dental root canals, and in particular dental root canal filling cones or points, and process of sterilizing such cones/points.

Description of Related Art

Dental root canal treatment generally involves three stages: shaping, cleaning and obturation (generally involving filling and sealing). The purpose of performing dental root canal treatment is to remove infected dental pulp tissue inside the pulp chamber and root canals, and to fill/seal the vacant space with a biocompatible material. More specifically, the ultimate objective of root canal treatment is to eliminate the infection inside the dental root system and to tightly seal or obturate, in three dimensions (3-D), the tiny openings at the end of the root canal, (referred in the profession as an apex).

Heretofore, root canal treatment processes involve placement of a root canal filling and/or sealing point or cone in a prepared root canal to plug the root canal, ideally in a manner to eliminate micro-leakage. Hereinafter, the term "point" and "cone" will be used interchangeably to refer to dental root canal filler/sealer.

The most commonly used root canal filling material for many years is a biocompatible latex compound commonly called Gutta Percha (GP), which comprises polyisoprene, or trans-polyisoprene with a chemical composition of 1,4-trans-polyisoprene (TPI). Other thermoplastic polyurethane based compounds may be adopted. The filling material is made into cone/point shape with different diameter sizes at the tip of the cone. When heated, the material will soften to flow at rather low temperature settings, typically starting at 60 to 80 degree Celsius. In this soften state, users (dentists or specialists known as endodontists) can mold/pack filling material all the way into root canal system for optimum obturation, filling and sealing effects. The filling material is chemically inert, and is therefore more biocompatible. Gutta Percha also hold its dimension quite well when change from heated liquid alpha phase to cooled solid beta stage.

Typically, the filling cones are supplied in bulk (with 50 to 100 cones within a plastic container) and are non-sterile. It has been long desired by endodontists (e.g., by pioneer endodontist Dr. Louis I. Grossman's standard) that these filling cones should be sterilized prior to insertion into root canals of in vivo teeth. Failure to completely sterilize the root canal sealing cone could lead to future bacteria colonization inside the root canal system, and re-infection and possible loss of the tooth. Due to the low melting temperature threshold for GP material, the most widely used and very effective heat based sterilization method such as heat steam autoclave is however off limits. Heretofore, throughout the years, clinicians and researchers have tried so-called "cold sterile" technique with different chemical agents, such as Sodium Hypochlorite, Glutaraldehyde, and Chlorhexidine. Research papers have shown that these agents require sufficient time to be adequate to achieve sterilizing effect, sometimes hours for these chemical agents to take effect. This raises two fundamental questions: (a) are these chemical agents bactericidal or bacteriostatic; and (b) are the results achieved by using these chemical agents simply disinfection or true sterilization. (Generally, disinfection and sterilization are both decontamination processes. Disinfection generally refers to the process of eliminating or reducing harmful microorganisms from inanimate objects and surfaces; sterilization generally refers to the process of killing substantially all microorganisms; these being the main difference between sterilization and disinfection.)

Furthermore, there also are additional issues concerning use of these chemical agents in daily clinical setting. (1) Chemical sterilization/disinfection has to be carried out in a treatment room, by the patient's chairside, just prior to use. The vapors of these chemical agents produce strong odors, and are considered harmful to the patient. (2) The root canal filling cones are generally supplied in bulk (e.g., 50 to 100 units in each pack) and in a non-sterile condition. Since the sterilization/disinfection process can take a long time, it raises a serious question whether dental clinicians and nurses are complying with sterile protocol in their busy practice. (3) Cold chemical sterilization process is traditionally considered as surface sterilizer. When a "cold sterilized" root canal filling cone had been inserted into a root canal, heated and melted for three-dimensional molding condensation and tight seal, the inside non-sterile core material of the filling cone will become exposed to the outside. As a result, the filling material becomes contaminated and non-sterile.

Still further, there is a problem that the material for root canal that includes mainly Gutta Percha is easily deteriorated due to sterilization.

There remains an unresolved need to provide Gutta Percha based root canal filling points/cones that are sterilized prior to shipment to the endodontists.

SUMMARY OF THE INVENTION

The present invention provides an improved root canal filling composition, and a dental root canal filling point/cone made of a material having such composition, which can substantially maintain its physical and chemical characteristics and shelf life after sterilization, and a process of sterilizing the point/cone prior to shipment to a user.

In one aspect of the present invention, the inventive root canal filling point/cone has a composition that comprises nanoparticles, which can withstand sterilization by gamma irradiation. In one embodiment, the cone is made of a compound that includes a plurality of base polymers of substantially equal amounts. In one embodiment, the compound is Gutta Percha based. In accordance with another aspect of the present invention, the Gutta Percha based cone is packaged and sterilized by irradiation prior to shipment to a user. In one embodiment of the present invention, the irradiation is gamma irradiation.

The present invention will be described herein-below in reference to the example of root canal filling points made of endodontic filling material including what is known as Gutta Percha, for example. However, it is understood that the present invention could be applied to root canal filling points based on other types of endodontic filler materials, currently known or future discovered, without departing from the scope and spirit of the present invention.

BRIEF DESCRIPTION OF THE DRAWINGS

For a fuller understanding of the nature and advantages of the invention, as well as the preferred mode of use, reference should be made to the following detailed description read in conjunction with the accompanying drawings. In the following drawings, like reference numerals designate like or similar parts throughout the drawings.

FIG. 1A is a schematic illustration of a single-taper root canal filling cone in accordance with one embodiment of the present invention; FIG. 1B is an orthogonal view of FIG. 1A.

FIGS. 4A to 4E are various views of a package for cones in accordance with another embodiment of the present invention; FIG. 4A being a top perspective view, FIGS. 4B and 4C being bottom perspective views; FIG. 4D being a partial top perspective view, and FIG. 4E being a photographic image.

DETAILED DESCRIPTION OF THE PREFERRED EMBODIMENTS

Figure 2:
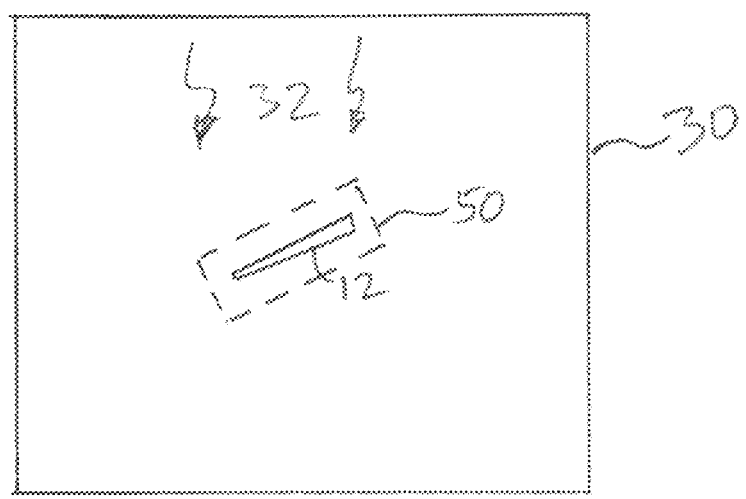
FIG. 2 is a schematic representation of gamma irradiation sterilization of a cone.
Figure 3A:
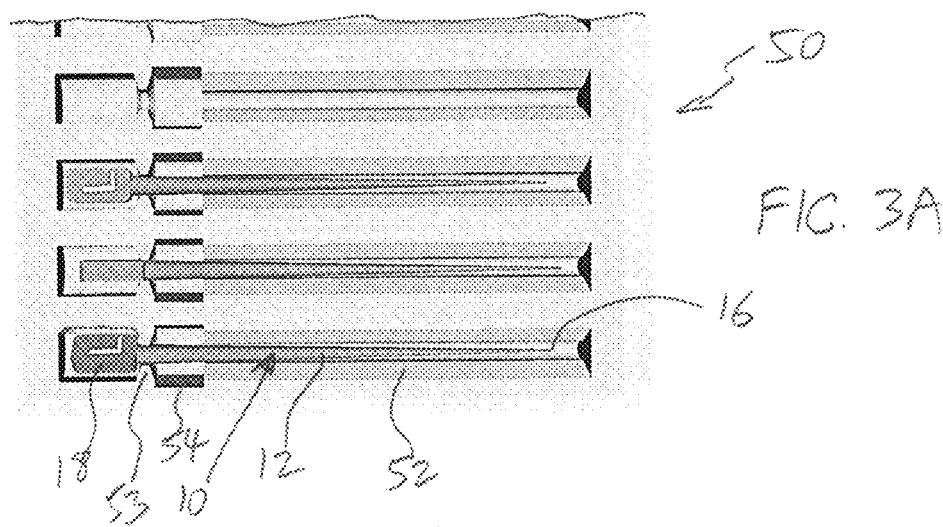
FIG. 3A to 3E are various partial views of a package for cones in accordance with one embodiment of the present invention.
Figure 3B:
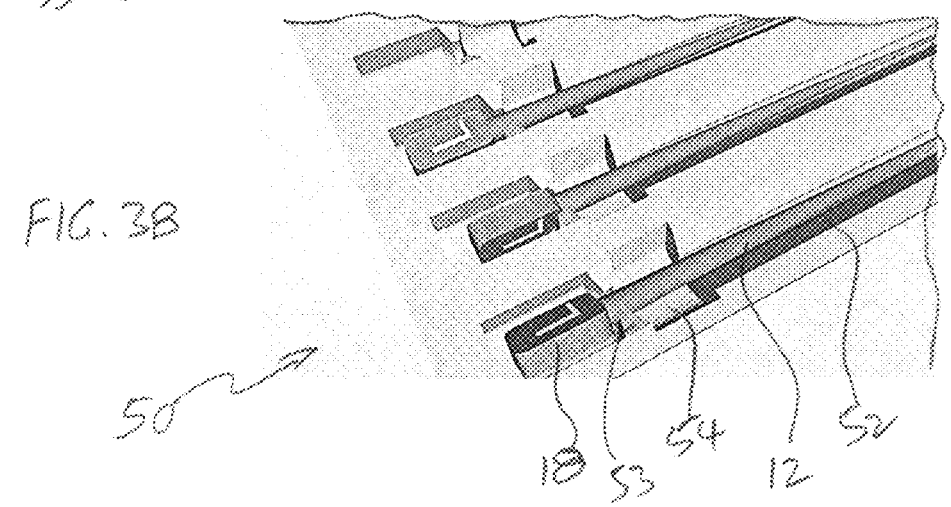
Figure 3C:
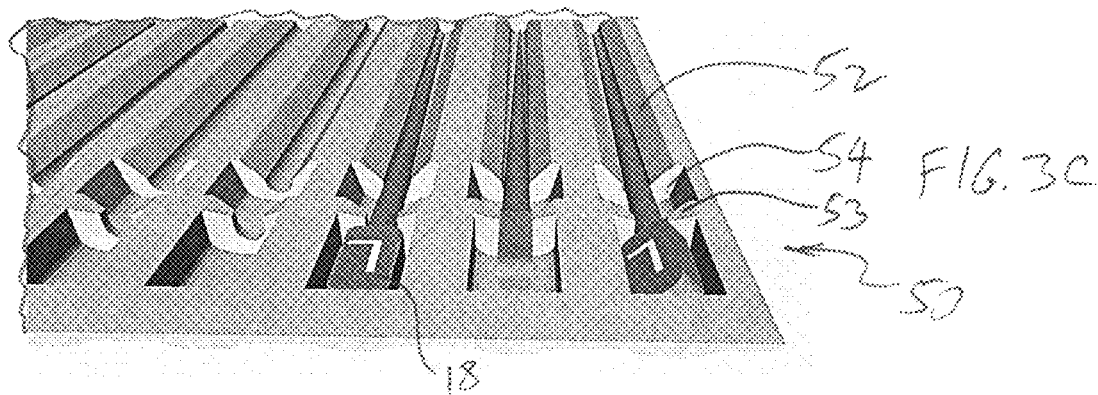
Figure 3D:
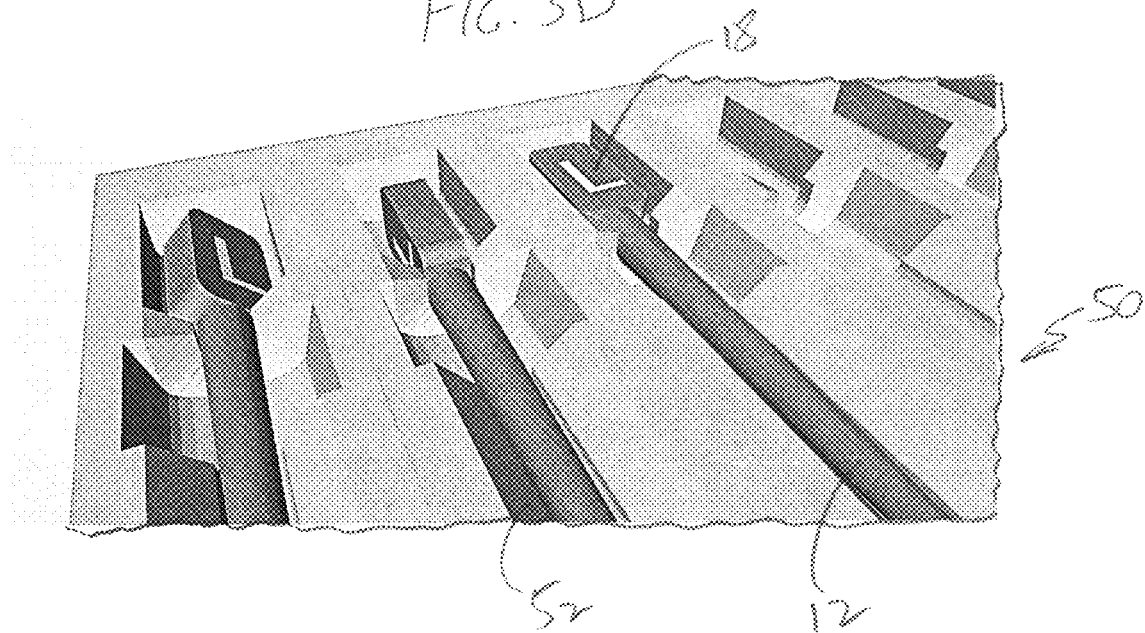
Figure 3E:
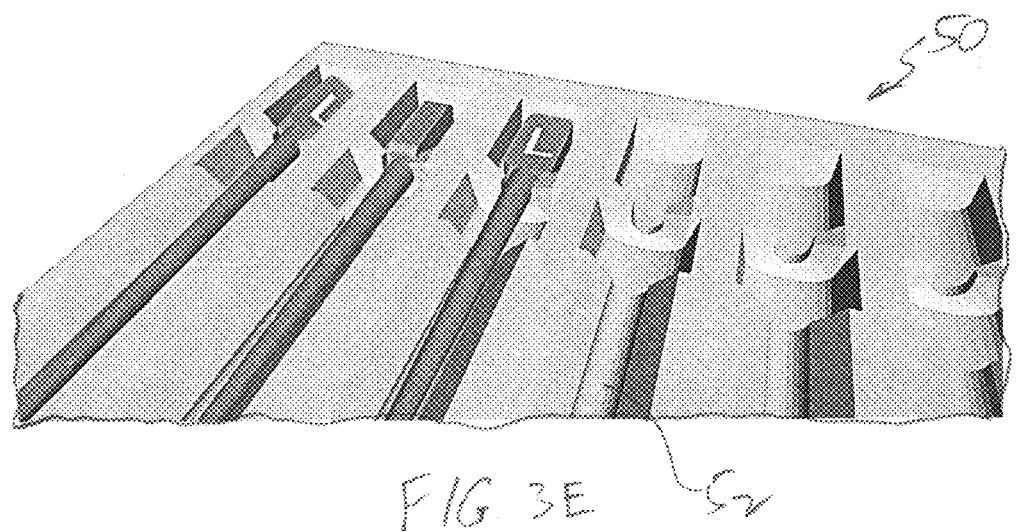

This invention is described below in reference to various embodiments with reference to the figures. While this invention is described in terms of the best mode for achieving this invention's objectives, it will be appreciated by those skilled in the art that variations may be accomplished in view of these teachings without deviating from the spirit or scope of the invention.

The present invention provides an improved root canal filling point/cone having a material that can maintain its physical and chemical characteristics and shelf life after sterilization, and a process of sterilizing the point/cone prior to shipment to a user.

In one aspect of the present invention, the inventive root canal filling point/cone composition comprises a compound that can withstand sterilization by gamma irradiation. In one embodiment, the compound is Gutta Percha based. In accordance with another aspect of the present invention, the Gutta Percha based cone is packaged and sterilized by gamma irradiation prior to shipment to a user. In one embodiment of the present invention, the irradiation is gamma irradiation.

The present invention will be described herein-below in reference to the example of root canal filling points made of endodontic filling material including what is known as Gutta Percha, for example. However, it is understood that the present invention could be applied to root canal filling points based on other types of endodontic filler materials, currently known or future discovered, without departing from the scope and spirit of the present invention. Further, while gamma irradiation is discussed by way of example below, it is understood that other form of appropriate irradiation may be effectively adopted for the sterilization process, without departing from the scope and spirit of the present invention.

FIGS. 1A and 1B illustrate a dental root canal filling cone (or point) 10 in accordance with one embodiment of the present invention. The cone 10 comprises a generally conical body 12 comprising a heat flowable material, such as Gutta Percha, which will be discussed further in detail below. The cone body 12 has a thick or large tail end 13 and a tapered thin or small tip end 16, which has a taper angle 15 that fits in the apex end of a prepared root canal cavity (the taper angle at the apex of the cavity being defined using a file tool known in the dentistry field). The diameter of each diametric section along the longitudinal axis of the body 12 is substantially circular, up to the large tail end 13. Extending beyond the large tail end 13 is a flat tab 18. An identification indicium 19 (e.g., alphanumeric) may be provided on the flat surface of the tab 18, to facilitate the user (dentist) to distinguish the particular configuration of the cone 10 (e.g., the indicia corresponds to a particular size, taper angle, material, etc.). During a dental root canal treatment process, the cone body 12 is inserted into the prepared root canal cavity. The tab 18 (along with excessive section of the body 12 that is not needed) can be removed by cutting before or after insertion. Heat is applied to the large end 13 using a heating tool (e.g., a heat gun). As the Gutta Percha material softens under the applied heat, the material flows in the root canal cavity to fill the root canal. Ideally, sufficient heat reaches the small end 16 of the cone 10 to flow the material to completely fill the apex of the root canal cavity.

The general dimensions of the body of the cone 10 may be within the following ranges, for example:
   a. Overall length L of cone 10: between 20 to 50 mm; or preferably between 25 to 35 mm.
   b. Diameter of the small tip end 16: between 0.01 to 0.3 mm; or preferably between 0.01 to 1.8 mm.
   c. Diameter of the large end 13: between 0.5 to 5 mm; or preferably between 0.8 to 2.5 mm.
   d. Taper angle: between 2° to 15°; or preferably between 4° to 12°.
   e. Length F of tab 18: between 3 to 5 mm; or preferably between 1.5 to 3.5 mm.
   f. Thickness H of tab 18: between 0.5 to 3 mm; or preferably between 0.8 to 2.8 mm.

Concerning the taper of the cone 10, the cone 10 may have a single taper angle for substantially its entire length (i.e., a single-taper cone as shown in FIG. 2), or a different taper angle for different longitudinal sections along its length (i.e., multi-taper cones, e.g., disclosed in U.S. Patent Application Publication No. US2014/0272802A1, which is a U.S. patent application filed by the inventor of the present invention, and which is incorporated by reference herein). In one embodiment, the multi-taper Gutta Percha cones each has a generally axisymmetric conical structure, wherein at least a section along the length of the Gutta Percha cone has a tapered structure, wherein the taper angle varies progressively in the axial direction to result in a multi-taper or variable taper conical structure. In one embodiment, the taper angles vary in small, discrete incremental steps along the length of the point, thus forming a structure having adjoining conical sections having different and discretely varying tapers at different axial sections along the length.

Further, as further discussed herein below, the conical point 10 may include nanoparticles to improve thermal conductive characteristics, as disclosed in U.S. Pat. No. 9,192,545, which is issued to the inventor of the present invention, and which is incorporated by reference herein.

In accordance with the present invention, the inventive root canal filling cones are made of a modified root canal filling material composition incorporating nanoparticles, which are sterilizable by applying a gamma irradiation protocol, without adversely affecting the integrity of the cones and will maintain adequate shelf life. In accordance with the present invention, by changing the Gutta Percha material characteristics by adding filler particles (e.g., nanoparticles and/or based on nanotechnology), and further appropriately changing the production and/or formulation process for the root canal filling composition, the gamma ray (Co-60) (or other known and/or commonly used irradiation sterilization techniques) can be used properly to irradiate bacteria and other biological contaminants, yet preserving the integrity of the material in terms of shelf-life and clinical features. FIG. 2 schematically illustrates sterilizing a cone 12 by subjecting it to gamma irradiation 32 in a chamber 30. For irradiation sterilization purpose, gamma ray power is measured as absorbed dose units, in KiloGray (kGy). The irradiation dosage may be in the range between 5 kGy and 20 kGy. Preliminary tests have shown that irradiation dosage in the range of 8 kGy to 13 kGy applied to dental Gutta Percha material can achieve desired sterilization result and yet preserve physical property of the product for intended use. This dosage range is also commonly used for sterilizing other medical disposable single use devices, such as syringes, needles, etc.

In accordance with Dr. Jerold Martin, he described gamma irradiation as follows: "Gamma rays are a form of electromagnetic radiation—like x-rays, but with higher energy. The primary industrial sources of gamma rays are radionuclide elements such as Cobalt 60, which emit gamma rays during radioactive decay. Gamma rays pass readily through plastics and kill bacteria by breaking the covalent bonds of bacterial DNA. They are measured in units called kiloGrays (kGy). Gamma irradiation provides a number of benefits in cost and sterility assurance. It can be applied under safe, well-defined, and controlled operating parameters, and is not a heat or moisture generating process. Consequently, there is no heat stress and condensate drainage or outgassing is not required. Most importantly, there is no residual radioactivity after irradiation."

Since dental root canal filling material is made of variety of polymer material, just like plastic polymer, gamma ray can certainly penetrate into root canal obturation cones, just like penetrating plastic layer as indicated by Dr. Jerold Martin, to sterilize these cones beyond the surface layer.

While gamma irradiation has been widely used in sterilizing hypodermic needles and syringes, it remains a challenge to effectively use gamma radiation to sterilize root canal filling cones by gamma radiation, given certain issues that must be overcome, as further explained herein below. The inventor realizes that applying gamma irradiation to traditional root canal filling cones could alter and/or destroy the polyisoprene and/or polyurethane molecule chains in the compound of the cones. As a result, it could significantly reduce the shelf life and adversely change the clinical performance of the cones. The present invention provides the solution to overcome those issues.

Heretofore, Gutta Percha root canal filling cones are primarily made by manual labor, using bare hands. Simply applying irradiation sterilization process to prior art Gutta Percha materials without addition filler particles (e.g., nanoparticle sized filler in accordance with the present invention) would damage the polymer molecule chains of the polymer material, and hence adversely affecting the physical integrity of the root canal filler point made with these prior art material without addition filler particles. These filler particles are beyond the regular inert biocompatible Zn Oxide filler found in prior art Gutta Percha based root canal filling composition, which are not nano-sized. This is due to the unstable nature of the polyisoprene and polyurethane polymers (different chain length mixed together randomly). Natural source based polymer also contains some protein based material, along with other impurities. Irradiation could carbonize protein impurities and leaving voids in the material. Irradiation also could break up the randomly mixed polymer chain sizes and causing major re-arranging or breaking down of the matrix structure.

In order to make these polymers more stable, one could select material with higher grade, and choose synthetics polyisoprene over natural polyisoprene. Higher grade polymer selection means choosing polymer with a very narrow range of polymer molecule chain length, measured with Mooney's Index. When this high grade polymer undergoes irradiation sterilization process, the polymer chain size change will be less and will be more uniformed. As a result, the polymer matrix could be preserved. However, choosing narrower polymer chain sizes is still not adequate to sustain and survive gamma irradiation treatment for sterilization. Other preservation mechanism will be needed to further stabilize polymer chains from gamma irradiation sterilization process.

In one embodiment, the present invention incorporates nanoparticles into a matrix material of the root canal filling points (which can be based on the prior invention disclosed in U.S. Pat. No. 9,192,545 and counterpart PCT patent application no. PCT/US13/42120, which were filed by the inventor of the present invention, and which are fully incorporated by reference herein). Nano sized filler particles bond polymer chains tightly together to form more orderly polymer chain meshing and therefore stronger matrix. Adding nano-sized particles into a compound will re-arrange the main components molecule alignment and will increase the strength of the final compound. This should protect the matrix and compound when going through the irradiation sterilization process. In one embodiment, the total ZnO nanoparticles may be between 5% to 20%, or less than 20%, 15% or 12%, by weight of the root canal filling composition. In one embodiment, the ZnO nanoparticles may comprise at least two groups of nanoparticles having substantially different size ranges. For example, the ZnO nano-particles may comprise a first group having significantly larger particle sizes in the range of 700-900 nm (e.g., between 5% to 20%, or less than 20%, 15% or 12%, by weight of the root canal filling composition), and a second group having significantly smaller particle sized in the range of 10 to 50 nm, or between 20 to 30 nm (e.g., between 0.1% to 1%, or less than 1%, 0.5%, 0.3% or 0.25%, by weight of the root canal filling composition).

The characteristic size (or the statistical average size) of the nanoparticles is on the order of 1000 nm or less (e.g., the particle diameter if spherical). In one embodiment, the characteristic size is 500 to 1000 nm. Some of the particles may have characteristic size on the order of 100 nm or less. According to nano-technology, nanoparticles exhibit properties that are not found in bulk samples of the same material. At the nano-scale, the physics of nanoparticles is such that their properties are different from the properties of the same material in larger, bulk form.

The characteristic size of the particles does not have to be uniform. All particles may be generally or substantially the same size, or have random sizes within the prescribed size range.

The particles may be made of high heat conductive metal, non-metal, organic or inorganic materials, including without limitations Zinc Oxide, Magnesium Silicate, gold, silver, titanium, diamond, etc. The matrix of base filling material may include natural or synthetic heat flowable polymeric materials that are bio-inert or bio-compatible when disposed in dental root canals, which may include rubber, thermoplastic or other polymeric materials. Rubber material may include trans-polyisoprene based material, such as Gutta Percha. In a specific embodiment, metallic nanoparticles are dispersed in dental Gutta Percha material. For example, Zinc Oxide nanoparticles are added to a matrix of dental Gutta Percha material to form a composite root canal filling material. Zinc Oxide nanoparticles in powder form are commercially available, with particle sizes in 700-900 nm, or smaller sizes of 100 nm, 75 nm, 50 nm, and 20 nm. Other sizes of nanoparticles could also work in accordance with the present invention.

In another embodiment of the inventive root canal filling composition, the polymer being utilized to form the cones shall have different viscosity at melting, or different molecule chain length groups to allow long chain group protecting short chain group from negative physical irritation from gamma irradiation sterilization process. The chain length is measured and referenced by Mooney index values as used in standard rubber industry. Tests show that by mixing each of at least the following Mooney specified Gutta Percha polymers within the total Gutta Percha group in the composition: Mooney 20 (ML20), Mooney 50 (ML50), and Mooney 100 (ML100), the resultant compound can adequately tolerate the irradiation sterilization process, and yet preserved adequate product characters for clinical application. For example, substantially (within +/−10% variation) equal amounts of the ML20, ML50 and ML100 may be mixed together (i.e., substantially one-third each of the different polymers, to represent substantially equal proportions of the different polymers within the compound). In one embodiment, the total Gutta Percha polymer may be less than 50%, 40%, 30%, 25% or 20% by weight of the root canal filling composition.

A weak link of this compound may be the plasticizers used during the production process. One element is the antioxidant agent. Because the two polymers (polyisoprene and polyurethane) used here have low temperature melting threshold, traditional selection of antioxidant has low temperature limitation as well. High temperature antioxidant should be used in order to protect the polymer compound against all physical irritations, including the irradiation process. Nano or near-nano sized particles of high temperature tolerant antioxidant (AO) agent performed better in preliminary tests and can also serve as plasticizer to render the dental Gutta Percha material to have a smooth handling characteristic (i.e., material flowability, which affects ease of shaping the cones, e.g., by hand-rolling or by injection molding). In one embodiment, the total AO may be between 0.25% to 2%, or less than 2%, 1%, 0.75% or 0.5%, by weight of the root canal filling composition. For example, the AO nanoparticles may have particle sizes in the range of 300-800 nm. In the inventive material, nanoparticles used as selective fillers can also function as polymer molecule chain protector against irradiation sterilization process and serve as plasticizer to make the finished compound smoother.

The root canal filling points can be made with the inventive filling material having metallic and non-metallic nanoparticles described above, using traditional roll processes or using the inventive injection molding process disclosed in U.S. Patent Publication No. 2014/0315155A1, which was filed by the inventor of the present invention, which is incorporated by reference herein.

Below is an example of the composition of the inventive root canal filling cone in accordance with one embodiment of the present invention:

| Component | Parts By weight | % By weight | Weight (g) |
| --- | --- | --- | --- |
| Gutta Percha-ML20 ** | 33.33 | 7.75% (+/−10% variation) | 333.33 |
| Gutta Percha-ML50 ** | 33.33 | 7.75% (+/−10% variation) | 333.33 |
| Gutta Percha-ML100 ** | 33.33 | 7.75% (+/−10% variation) | 333.33 |
| Wax | 2 | 0.46% | 20.0 |
| AntiOxidant (AO)-High T, 300-800 nm particle size | 2 | 0.46% | 20.0 |
| Nano ZnO 20-30 nm particle size | 1 | 0.23% | 10.0 |
| BaS04 (radiopaque)-Barium Sulphate | 60 | 13.95% | 600.0 |
| ZnO (inert biocompatible filler; not nano-sized) | 212.5 | 49.42% | 2125.0 |
| Color Yellow | 3.3 | 0.77% | 33.0 |
| Color Red | 0.2 | 0.05% | 2.0 |
| Nano ZnO 700-900 nm particle size | 49 | 11.38% | 490 |
| Total: | 430 | 100% | 4300 |

**For different desired clinical and handling characteristics (the material flowability), different relative proportion of Moony index Gutta Percha may be used, with the interrelating percentages altered at plus and minus 10% range without adversely affecting sterilability and product integrity. For example, if one wants to increase GP-ML20 by 10%, then one can reduce only GP-ML50 by 10%, or reduce 5% each for GP-ML50 and GP-ML100.

In order to fully utilize the full potential for sterilized Gutta-Percha cones having the above composition, a modified material processing procedure was developed. In accordance with one embodiment, a first batch of ingredients are mixed, including Gutta-Percha Mooney 20, non-metallic nano zinc oxide (ZnO) particles of 20-30 nm, nano Antioxident (AO), and wax. Then a second batch of ingredients including Gutta-Percha Mooney 50 and Mooney 100, plus Zinc Oxide particles of 800-900 nm. This will ensure GP molecule chains are thoroughly mixed together and tightly locked down with the zinc oxide nanoparticles. Wax serves as plasticizer and is unstable, as it would be "burned off" by gamma irradiation and weakens the entire Gutta Percha compound. In one embodiment, the total wax may be between 0.25% to 2%, or less than 2%, 1% or 0.5%, by weight of the root canal filling composition. By adding these ingredients first, it facilitates the mixing process, yet all polymers are locked and protected by nanoparticles. All other remaining ingredients are added at the same time in the middle of the mixing process.

The end result is a new composition of a compound that can withstand Gamma irradiation sterilization process and yet will not lose its physical and chemical characters and shelf life. The inventive material renders possible irradiation sterilization of dental root canal filling material/cones without altering the base matrix material (e.g., synthetic or natural Gutta Percha) itself. The irradiation sterilization (e.g., by gamma rays) can be performed by the manufacturer or packager of the cones, before shipping to the end user. At the end, dentists will have pre-sterilized product for use in performing root canal treatments. This would improve sterilization standard, reduce clinical confusion, and minimize the risk of non-compliance in everyday patient care.

In another aspect of the present invention, the inventive root canal filling cones is sterilized after packaging, e.g., using a blister seal packaging commonly adopted for packaging, e.g., medication. Gamma irradiation can penetrate the packaging material to sterilize the cones contained within the sealed packaging without breaking the seal, with its contents, i.e., sterilized cones, protected by the sealed packaging to remain sterilized.

Heretofore, root canal filling cones are customarily packaged as "bulk pack" with 50 to 100 cones in a container. However, a dentist typically uses 5 to 10 cones for one root canal treatment. If the inventive cones irradiation sterilized in accordance with the present invention were to be packaged in a 50 to 100-unit bulk pack, once it is opened (i.e., the seal broken) for the first use, the rest of the cones will be exposed to the environment and risk becoming non-sterile. In accordance with one embodiment of the present invention, packaging of the inventive filling cones is in the form of individual single use, sealed packs.

Referring to FIGS. 3A to 3E, 4A to 4E and 5, various embodiments of sealed, single used packaging are illustrated. The overall packaging resembles blister packaging known in the art for packaging syringes, needles, chewing gum, etc. However, in accordance with the present invention, the blister packaging is provided with a support that secures the position of the body 12 of the cone 10 within the package, to prevent it from knocking against the inside wall of the package, which could damage the delicate tip 16 that was formed with a precise taper angle 15 (e.g., by injection molding). Specifically, FIGS. 3A to 3E (and referring also to FIGS. 1A and 1B) illustrate an embodiment in which a plurality of trenches 52 are provided that each receive a cone body 12. The tab 18 at the tail end 13 of the cone body 12 is held against a stop 53 in the trench 52, to prevent the cone body 12 from moving relative to the trench in the direction of its axis. The section right below the tab 18 is held against a complementary opening in the stop 53 by an interference fit (or mechanical fit), to prevent the cone body 12 from coming loose out of the trench 52. A user can pick the cone 10 out of the trench 52 by picking the tab 18 with a pair of tweezers. Alternatively, the well 54 that defines the stop 53 provides additional clearance for receiving the tips of a tweezer used to pick the cone 10 out of the trench 52. The package 50 includes a plastic sheet (not shown in the figures to avoid obscuring the features within the package), preferably transparent, seals the trenches 52.

Figure 4A:
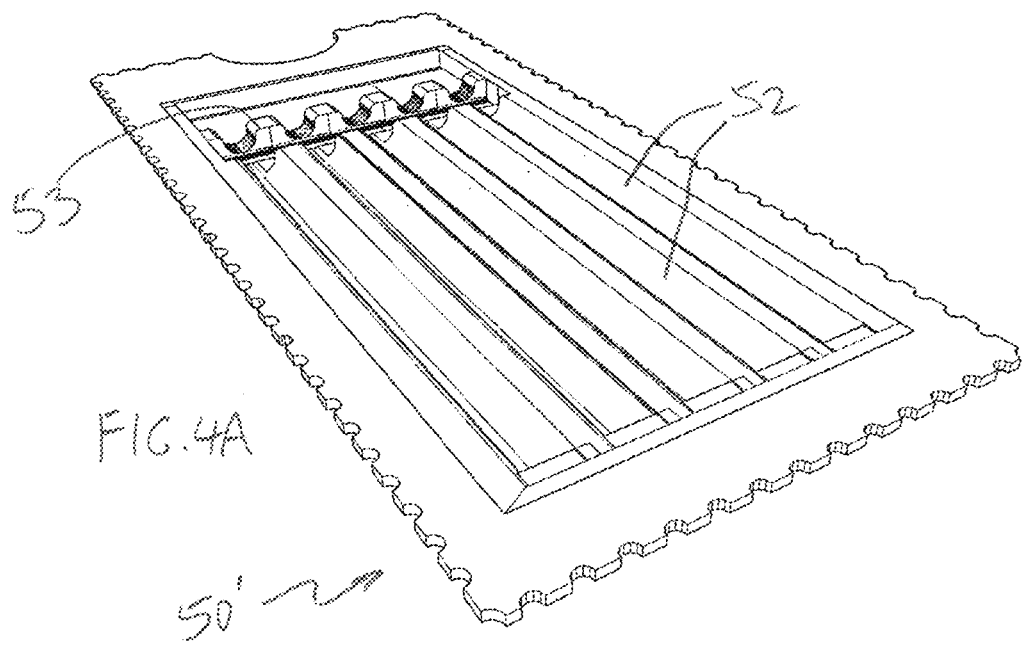
Figure 4B:
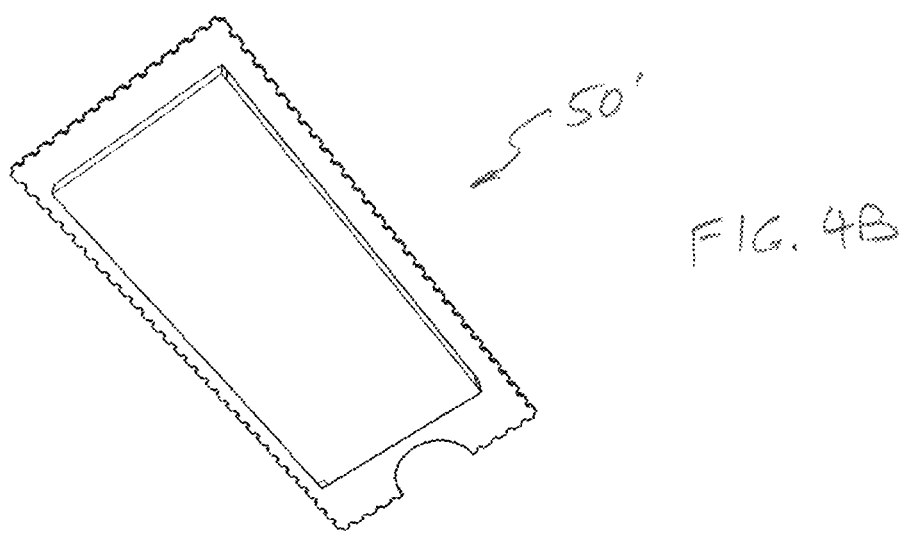
Figure 4E:
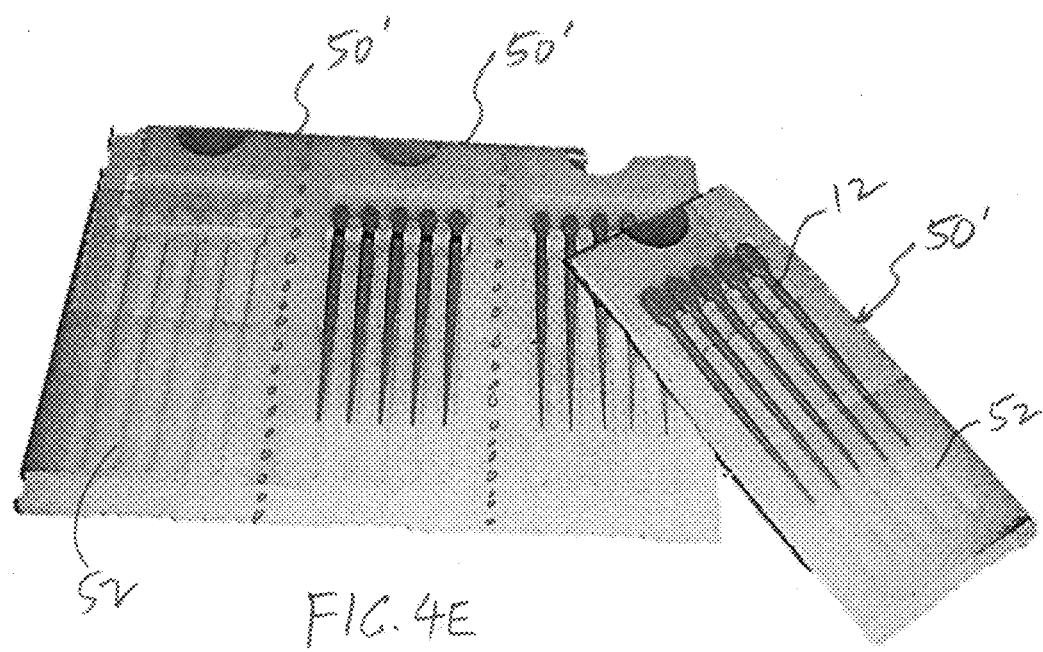
Figure 5:
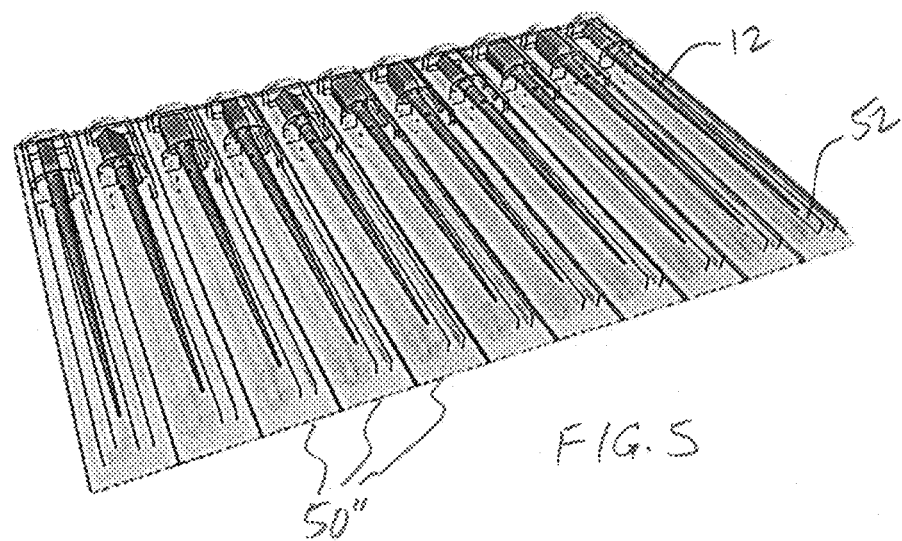
FIG. 5 is a bottom view of a package for cones in accordance with a further embodiment of the present invention.

The embodiments of FIGS. 4A to 4E and FIG. 5 share similar structure within the package. In the embodiment of FIGS. 4A to 4E, each sealed package 50' is configured to package five cones 10. A plurality of packages 50' are joined as a flat as shown in FIG. 4D, with a row of perforations provided between adjoining packages 50' to facilitate separation of the individual packages. FIG. 4E is a photographic image showing one of the packages broken off from the flat. For simplicity, the sealing top layer is not shown in FIG. 4. FIG. 5 illustrates a flat of single-cone packages 50", each having a similar trench having similar features. Adjacent packages 50" are connected by an adjoining section having a row of perforations to facilitate separation of the individual packages.

The seal packages 50, 50' and 50" containing cones may be placed in the chamber 30 for sterilization by irradiation of gamma rays. The packages may be made of paper or plastic material (e.g., PVC) known to allow gamma irradiation to penetrate the package material to sterilize the contents therein.

While the present invention has been described above in connection with the illustrated embodiments, the scope of patent invention covers all possible present and future variations and improvements that is apparent from the disclosure above. While the invention has been particularly shown and described with reference to the preferred embodiments, it will be understood by those skilled in the art that various changes in form and detail may be made without departing from the spirit, scope, and teaching of the invention. Accordingly, the disclosed invention is to be considered merely as illustrative and limited in scope only as specified in the appended claims.

REFERENCES

Cold sterilization of gutta-percha cones with formocresol vapors. E S Senia, R V Marraro and J L Mitchell, Journal of the American Dental Association (May 1, 1977) 94, 887-890.

Rapid sterilization of gutta-percha cones with 5.25% sodium hypochlorite Journal: J Endod; Senia E S, Marraro R V, Mitchell J L, Lewis A G, Thomas L.

The Rapid Sterilization of Gutta-Percha Cones with Sodium Hypochlorite and Glutaraldehyde; J Endod 2006; 32:1202-1204; Nurhan Ozalp, Zeynep Okte, Berrin Ozcelik Disinfection of gutta-percha cones with chlorhexidine and sodium hypochlorite; Oral Surg Oral Med oral Pathol oral Radiol Endod 2005; 100:512-7.

Efficacy of chemical sterilization and storage conditions of gutta-percha cones; Int Endod J. 2001 September; 34(6): 435-9; DA Motta P G, de Figueiredo C B, Maltos S M, etc.

Understanding Gamma Sterilization; Feb. 1, 2012; By Jerold Martin; BioPharm International; Volume 25, Issue 2.

AAMI/ANSI/ISO 11137:2006, "Sterilization of health care products—Radiation—Part 1: Requirements for the development, validation and routine control of a sterilization process for medical products; Part 2: Establishing the sterilization dose; Part 3: Guidance on dosimetric aspects," (2006).

I claim:

1. A root canal filling composition, comprising:
   a plurality of Gutta Percha polymers having different Mooney index values;
   an antioxidant of particles having a particle size of 1000 nm or less; and
   a filler of particles having a particle size of 1000 nm or less,
   wherein the composition can substantially maintain its physical and chemical characteristics and shelf life after sterilization by irradiation.

2. The composition as in claim 1, wherein the plurality of Gutta Percha polymers comprise at least three Gutta Percha polymers, each having a different Mooney index values.

3. The composition as in claim 2, wherein the plurality of Gutta Percha polymers comprise Gutta Percha polymers having at least Mooney index values of 20, 50 and 100.

4. The composition as in claim 3, wherein the plurality of Gutta Percha polymers comprise about equal proportions of Gutta Percha having the different Mooney index values.

5. The composition as in claim 1, wherein the filler comprises at least two groups of filler particles having substantially different particle sizes.

6. The composition as in claim 5, wherein the filler comprises a first group of filler particles having a particle size of about 20-30 nm.

7. The composition as in claim 6, wherein the first group of filler particles is less than 0.3% by weight of the composition.

8. The composition as in claim 5, wherein the filler comprises a second group of filler particles having a particle size of 700-900 nm.

9. The composition as in claim 8, wherein the second group of filler particles is less than 15% by weight of the composition.

10. The composition as in claim 5, wherein the antioxidant comprises particle sizes of 300-800 nm.

11. The composition as in claim 10, wherein the antioxidant is less than 1% by weight of the composition.

12. A root canal filling composition, comprising:

| Component | Parts By weight | % By weight | Weight (g) |
|---|---|---|---|
| a first Gutta Percha polymer | 33.33 | 7.75% (+/−10% variation) | 333.33 |
| a second Gutta Percha polymer | 33.33 | 7.75% (+/−10% variation) | 333.33 |
| a third Gutta Percha polymer | 33.33 | 7.75% (+/−10% variation) | 333.33 |
| Wax | 2 | 0.46% | 20.0 |
| an antioxidant - High T, 300-800 nm particle size | 2 | 0.46% | 20.0 |
| Nano ZnO 20-30 nm particle size | 1 | 0.23% | 10.0 |
| BaSO$_4$ | 60 | 13.95% | 600.0 |
| (radiopaque) ZnO (inert biocompatible filler; not nano-sized) | 212.5 | 49.42% | 2125.0 |
| Color Yellow | 3.3 | 0.77% | 33.0 |
| Color Red | 0.2 | 0.05% | 2.0 |
| Nano ZnO 700-900 nm particle size | 49 | 11.38% | 490 |
| Total: | 430 | 100% | 4300. |

13. A cone for a dental root canal filling, comprising:
a body having a generally axisymmetric conical structure, wherein at least a section along the body has a tapered structure, wherein the body is made of a material having a composition as claimed in claim 1.

14. A method of sterilizing a cone for dental root canal filling as claimed in claim 13, comprising:
subjecting the cone to irradiation.

15. The method of claim 14, wherein the cone is subject to gamma radiation.

16. The method of claim 15, further comprising sealing the cone in a package prior to subjecting the package containing the cone to gamma irradiation.

17. The method of claim 16, wherein the gamma irradiation is in the range between 5 kGy to 20 kGy.

18. The method of claim 17, wherein the gamma irradiation is in the range between 8 kGy to 13 kGy.

* * * * *